US007973005B2

(12) United States Patent
Bauer

(10) Patent No.: US 7,973,005 B2
(45) Date of Patent: Jul. 5, 2011

(54) ALPHA-1 ANTITRYPSIN FOR TREATING EXACERBATION EPISODES OF PULMONARY DISEASES

(75) Inventor: Shabtai Bauer, Jerusalem (IL)

(73) Assignee: Kamada Ltd., Ness-Ziona (IL)

( * ) Notice: Subject to any disclaimer, the term of this patent is extended or adjusted under 35 U.S.C. 154(b) by 0 days.

(21) Appl. No.: 12/278,756

(22) PCT Filed: Feb. 8, 2007

(86) PCT No.: PCT/IL2007/000181
§ 371 (c)(1),
(2), (4) Date: Nov. 24, 2008

(87) PCT Pub. No.: WO2007/091266
PCT Pub. Date: Aug. 16, 2007

(65) Prior Publication Data
US 2009/0131305 A1 May 21, 2009

Related U.S. Application Data

(60) Provisional application No. 60/773,654, filed on Feb. 16, 2006, provisional application No. 60/771,465, filed on Feb. 9, 2006.

(51) Int. Cl.
*A61K 31/00* (2006.01)
*A61K 38/00* (2006.01)
(52) U.S. Cl. .......................... 514/1; 514/1.5
(58) Field of Classification Search .................... None
See application file for complete search history.

(56) References Cited

U.S. PATENT DOCUMENTS

| 5,093,316 | A | 3/1992 | Lezdey et al. .................. 514/8 |
| 5,518,179 | A | 5/1996 | Humberstone et al. .... 239/102.2 |
| 5,618,786 | A | 4/1997 | Roosdorp et al. ............... 514/8 |
| 5,780,440 | A | 7/1998 | Lezdey et al. .................. 514/21 |
| 6,462,180 | B1 * | 10/2002 | Lebing et al. ................ 530/395 |
| 6,655,379 | B2 | 12/2003 | Clark et al. ............... 128/203.12 |
| 2008/0060640 | A1 | 3/2008 | Waldner et al. .......... 128/200.16 |

FOREIGN PATENT DOCUMENTS

| DE | 199 53 317 C1 | 2/2001 |
| WO | WO 01/34232 A1 | 5/2001 |
| WO | WO 03/026832 A1 | 4/2003 |
| WO | WO 2004/014569 A1 | 2/2004 |
| WO | WO 2004/052436 A1 | 6/2004 |
| WO | WO 2005/027821 A2 | 3/2005 |
| WO | WO 2005/048985 A2 | 6/2005 |
| WO | WO 2005/086915 A2 | 9/2005 |

OTHER PUBLICATIONS

International Search Report PCT/IL2007/000181 Dated Sep. 21, 2007.
R. Hubbard et al., *Anti-Neutrophil-Elastase Defenses Of The Lower Respiratory Tract In a 1-Antitrypsin Deficiency Directly Augmented With An Aerosol of a 1-Antitrypsin*, Aug. 1, 1989, pp. 206-212, Annals of Internal Medicine, vol. 3, No. 3.
P. Brand et al., *Alveolar Deposition Of Monodisperse Aerosol Particles In The Lung Of Patients With Chronic Obstructive Pulmonary Disease*, Jan./Aug. 2002, Abstract, Experimental Lung Research, vol. 28, No. 1.
P. Brand et al., *Peripheral Deposition Of Alpha1-Protease Inhibitor Using Commercial Inhalation Devices*, Aug. 2003, Abstract, European Respiratory Journal, vol. 22, No. 2.
G. Hansen et al., *Alpha-1-Proteinase Inhibitor Abrogates Proteolytic And Secretagogue Activity Of Cystic Fibrosis Spectrum*, 1995, Abstract, Respiration, vol. 62, No. 3.
International Search Report, application No. PCT/IL2007/000182, dated Oct. 5, 2007.
K. Kawabata et al. "Delayed Neutrophil Elastase Inhibition Prevents Subsequent Progression of Acute Lung Injury Induced by Endotoxin Inhalation in Hamsters", American Journal of Respiratory And Critical Care Medicine, vol. 161, pp. 2013-2018 (2000).
S. Yasui et al., "A Specific Neutrophil Elastase Inhibitor (ONO-5046-Na) Attenuates LPS-Induced Acute Lung Inflammation In The Hamster", European Respiratory Journal, vol. 8, pp. 1293-1299 (1995).
Z. Jie et al., "Protective Effects Of $\alpha_1$-Antitrypsin On Acute Lung Injury In Rabbits Induced By Endotoxin", Chinese Medical Journal (English), vol. 116(11), pp. 1678-1682 (2003).

* cited by examiner

*Primary Examiner* — Nashaat Nashed
(74) *Attorney, Agent, or Firm* — Winston & Strawn LLP

(57) ABSTRACT

The present invention relates to methods for the treatment of exacerbation periods of pulmonary diseases, particularly chronic obstructive pulmonary diseases, by administering alpha-1 antitrypsin (AAT) to a subject in need thereof. Particularly, the present invention discloses the efficient treatment of exacerbation periods of pulmonary diseases by administering AAT via inhalation.

15 Claims, No Drawings

ALPHA-1 ANTITRYPSIN FOR TREATING EXACERBATION EPISODES OF PULMONARY DISEASES

This application is a 371 filing of International Patent Application PCT/IL2007/000181 filed Feb. 8, 2007, which claims the benefit of application Nos. 60/771,465 filed Feb. 9, 2006 and 60/773,654 filed Feb. 16, 2006.

FIELD OF THE INVENTION

The present invention relates to methods for treatment of exacerbation periods of pulmonary diseases, particularly chronic obstructive pulmonary diseases, by administering alpha-1 antitrypsin (AAT), and particularly by administering AAT by inhalation.

BACKGROUND OF THE INVENTION

Chronic Obstructive Pulmonary Diseases (COPD)

A chronic obstructive pulmonary disease (COPD) is a disease state characterized by airflow limitation that is not fully reversible. The airflow limitation is usually progressive and associated with an abnormal inflammatory response of the lung to noxious particles or gases. Symptoms, functional abnormalities and complications of COPD can be attributed to this underlying phenomenon of abnormal inflammatory response and to processes related thereto.

The chronic airflow limitations characteristic of COPD is caused by a mixture of small airway disease (obstructive broncholitis) and parenchymal destruction (emphysema), the relative contribution of each vary from person to person. Chronic inflammation causes remodeling and narrowing of the small airway. Destruction of the lung parenchyma, also by inflammation processes, leads to the loss of alveolar attachments to the small airways and decrease the lung elastic recoil; these changes diminish the ability of the airways to remain open during expiration.

In addition to inflammation, two other processes are thought to be important in the pathogenesis of COPD: imbalance of proteinases and antiproteinases in the lung, and oxidative stress. These processes may themselves be consequences of inflammation, or they may arise from environmental (e.g., oxidant compounds in cigarette smoke) or genetic (e.g. alpha-1 antitrypsin deficiency) factors.

The progressive course of COPD is complicated by exacerbation episodes that have many causes and occur with increasing frequency as the disease progresses. The most common causes for an exacerbation are infection of the tracheobronchial tree and air-pollution, but the cause of about one third of monitored severe exacerbations cannot be identified. The effect of exacerbations may be more apparent in patient with mild to moderate disease and an increasing number of exacerbations has been shown to correlate with the decline in gas transfer during expiration. Exacerbations may be treated at home, but very often require medical intervention and hospitalization. Hospital mortality of patients admitted for an exacerbation of COPD is approximately 10%, and the long-year survival is poor. Mortality reaches 40% in one year, and rates are even higher (up to 59%) for patients older than 65 years (GOLD global strategy for diagnosis, management, and prevention of COPD, updated 2004).

Alpha-1 Antitrypsin and Lung Diseases

Alpha-1 Antitrypsin (AAT), also known as Alpha-1-Proteinase Inhibitor (API) and Serine Protease Inhibitor, is a plasma-derived protein belonging to the family of serine proteinase inhibitors. AAT is synthesized primarily in the liver, and to a lesser extent in other cells, including macrophages, intestinal epithelial cells and intestinal Paneth cells. In the liver, AAT is initially synthesized as a 52 kD precursor protein that subsequently undergoes post translational glycosylation at three asparagine residues, as well as tyrosine sulfonation. The resulting protein is secreted as a 55 kD native single-chain glycoprotein. AAT has a role in controlling tissue destruction by endogenous serine proteinases, and is the most prevalent serine proteinase inhibitor in blood plasma. AAT inhibits, inter alia, trypsin, chymotrypsin, various types of elastases, skin collagenase, renin, urokinase and proteases of polymorphonuclear lymphocytes.

AAT deficiency is a genetic condition that increases the risk of developing a variety of diseases including pulmonary emphysema (Laurell and Eriksson Scand J Clin lab Inves 1963. 15:132-140). It is caused by mutations in the AAT encoding gene (proteinase inhibitor (Pi) gene). Over 100 different allelic variants of the Pi genotype are recognized, of which 34 were found to be associated with a quantitative or functional deficiency of circulating AAT. There is currently no fully accepted explanation for this genetic variation of the Pi gene (Sandhaus RA Thorax 2004. 59:904-909).

One of the endogenous roles of AAT is to regulate the activity of neutrophil elastase, which breaks down foreign proteins present in the lung. In the absence of sufficient quantities of AAT, the elastase breaks down lung tissue, which over time results in chronic lung tissue damage and emphysema. The consequence of the low levels of AAT in the lower respiratory tract epithelial lining fluid of individuals with AAT deficiency is an insufficient antineutrophil elastase protective screen of the lung, such that a neutrophil elastase is able to act unimpeded to attack and destroy alveolar structures. The resulting lung damage is greatly accelerated by cigarette smoking, and is irreversible.

Based on the pathology of AAT deficiency it has been postulated that an imbalance between proteinases and antiproteinases results in lung destruction, wherein the imbalance may involve either increased production or activity of proteinases, or inactivation or reduced production of anti-proteinases. In subjects with normal AAT activity, the imbalance may be a consequence of the inflammation induced by inhalational exposure to harmful substances, oxidative stress and possibly other COPD risk factors.

It has been suggested that the sustained damage to lung tissue due to the imbalance between proteinases and antiproteinases, even if modest, leads to failure of the lung tissues to clear infection and engenders a cycle of repeat exacerbations and incremental damage. This course of events emphasizes the importance of avoiding repeated exacerbations, even of minor lung inflammation. Needham and Stockley (Thorax 2004. 59:441-445) found that 54% of 254 AAT-deficient patients studied showed one or more exacerbation episodes within 12 months. Most AAT patients associated with COPD have two to three exacerbation periods per year, one third of which are associated with viral infections (Anthonisen N R. N 2002. Engl J. Med. 347(7):526-527; Needham, 2004, supra). It has been shown that exacerbation periods correlated with deterioration in the pulmonary function. This phenomenon is fully consistent with the clinical picture observed in many AAT deficient subjects, which show repeated episodes of exacerbations of the upper respiratory tract, pulmonary infections and deteriorating pulmonary function over time.

Therapeutic Use of AAT

AAT is currently used therapeutically for the treatment of pulmonary emphysema in AAT-deficient patients. Purified AAT has been approved for replacement therapy (also known as "augmentation therapy") in such patients.

AAT in aerosolized route has also been proposed as a treatment for cystic fibrosis (CF) patients who suffer from recurrent endobronchial infections and sinusitis. The major cause of morbidity and mortality among CF patients is lung diseases. CF patients carry a mutation in the CFTR gene, resulting in a malfunctioning CTFR protein, defective water and salt transport and the ensuing thick secretions in the lung. The membrane defect caused by the CFTR mutation leads to chronic lung inflammation and infection. In normal individuals, elastase secreted by neutrophils in response to infection is neutralized by AAT. AAT is known to penetrate into pulmonary tissue and exert its activity within this tissue. In patients with CF, however, the unregulated inflammatory response overwhelms the normal protease (elastase)/antiproteinase (AAT) balance. The abnormal cycle is destructively self-perpetuating and leads to the accumulation of elastase in the lung and ultimately to tissue damage, destruction of the lung architecture, severe pulmonary dysfunction and, ultimately, death. Supplemental AAT may reduce the deleterious effects associated with excessive amounts of elastase. It has been recently shown that inhalation of AAT by CF patients increased the AAT levels and decreased elastase activity levels, neutrophils, pro-inflammatory cytokines and numbers of *Pseudomonas*, but had no effect on lung function (Matthias G. et al., ERJ Express. 2006. DOI: 10.1183/09031936.00047306).

International application WO 2005/027821 to the applicant of the present invention teaches a novel composition of purified, stable, active alpha-1 antitrypsin (AAT) for intravenous administration and inhalation, a process for its preparation and its use for treating pulmonary disease, including pulmonary emphysema and CF associated lung disease or disorder. The contents of WO 2005/027821 are incorporated herein by reference in their entirety.

AAT is currently administered intravenously. For example, the Aralast®, Zemaira®, Prolastin®, Trypsone® and Alfalastinbrands of human AAT are intravenous formulations indicated for augmentation therapy in patients having congenital deficiency of AAT with clinically evident emphysema.

Although the use of augmentation therapy has undoubtedly contributed to the well-being and improved life quality of AAT deficient subjects, serious problems in the disease management still remain. In addition to the uncertainty of the therapy efficacy, there is a limited availability of AAT, particularly as the use of intravenous replacement requires relatively large amounts of the protein. Augmentation therapy may result in reduced frequency and severity of exacerbation periods as a result of moderating the decline in lung function in certain patients; however, it does not provide appropriate means for treating AAT deficient patients during the exacerbation period.

It has been shown that in most cases the morbidity experienced by AAT deficient patients is mainly the result of the exacerbation rather than of the disease itself. Therefore, there is considerable clinical need for a treatment that can provide an adequate response to the patient's condition, rather than just providing symptomatic treatment, and prevent the potentially accelerated decline of the patients' health due to the exacerbation.

The GOLD (Global Initiative for Chronic, Obstructive, Lung Disease) organization has issued recommendations as to the management of COPD diseases in general, which include, inter alia, the prevention and treatment of exacerbation episodes.

Thus, there is an unmet need for, and it would be highly advantageous to have means for treating pulmonary diseases during exacerbation periods, in AAT-deficient as well as in normal AAT producing subjects.

SUMMARY OF THE INVENTION

The present invention relates to methods for treating pulmonary diseases during periods of exacerbation. Particularly, the present invention provides methods for treating pulmonary diseases, including pulmonary diseases associated with α-1 antitrypsin (AAT) deficiency, by administering AAT via inhalation.

The present invention discloses for the first time that exacerbation periods of pulmonary diseases can be treated effectively by administering to the lungs of a subject in need thereof a therapeutically effective amount of AAT, particularly by administering the AAT via inhalation. The AAT inhalation can be administered as the sole therapy, or in addition to intravenous AAT augmentation therapy.

Thus, according to one aspect, the present invention provides a method for treating an exacerbation of a pulmonary disease or disorder, comprising administering to the lungs of a subject in need thereof a therapeutically effective amount of Alpha-1 antitrypsin (AAT). According to one embodiment, the AAT is administered to the lungs by inhalation.

According to certain embodiments, the pulmonary disease or disorder is selected from the group consisting of emphysema, chronic obstructive pulmonary disease (COPD), bronchiectasis, (chronic dilatation of the bronchial tubes), parenchymatic and fibrotic lung diseases or disorders including cystic fibrosis, interstitial pulmonary fibrosis and sarcoidosis, tuberculosis and pulmonary diseases secondary to HIV.

According to other embodiments, the pulmonary disease or disorder is associated with AAT-deficiency. According to one embodiment, the pulmonary disease is congenital emphysema.

The AAT can be of a variety of different forms, including purified naturally occurring AAT and a recombinant AAT.

According to certain embodiments, the AAT is purified from a partially purified mixture of proteins by a process comprising chromatography on a plurality of ion exchange resins, as disclosed in International Application WO 2005/027821 to the Applicant of the present invention. As disclosed in that invention, the AAT is preferably purified from a partially purified mixture of proteins by a process comprising chromatography on at least two anion exchange resins and at least one cation exchange resin.

According to one embodiment the purified AAT is at least 90% pure. According to preferred embodiments the purified AAT is at least 95%, more preferably at least 99% pure. According to some embodiments, at least 90% of the AAT is in its active form.

According to certain embodiments, the AAT is formulated to form a pharmaceutical composition. According to one embodiment, the pharmaceutical composition is in the form of an aqueous solution. According to another embodiment, the pharmaceutical composition is in the form of a powder. According to a further embodiment, the pharmaceutical composition is devoid of a stabilizer. According to one currently preferred embodiment, the pharmaceutical composition comprising the purified AAT is in the form of a ready-to-use aqueous sterile solution. According to one embodiment, the pH of the composition is in the range of 6.5-7.5.

The present invention is based in part on the discovery that pulmonary delivery of AAT is efficient and effective for treating pulmonary diseases in general, and exacerbations of respiratory symptoms in particular. Without wishing to be bound by any particular theory or mechanism of action this efficacy may be attributed to the direct delivery of AAT to its site of action, such that effective amounts of active AAT are readily reached in this site to overcome the acute imbalance in proteinase/antiproteinase ratio developed during the exacerbation period.

To be administered by inhalation, the AAT is conveniently delivered in the form of an aerosol spray, from a pressurized pack or a nebulizer. The aerosolized AAT formulation may be in the dry powder form, it may be a solution, suspension or slurry to be nebulized, or it may be in admixture with a suitable low boiling point, highly volatile propellant, e.g., dichlorodifluoromethane, trichlorofluoromethane, dichlorotetrafluoroethane or carbon dioxide. In the case of a pressurized aerosol, the dosage unit may be determined by providing an apparatus comprising a valve to deliver a metered amount. According to certain embodiments, the methods of the present invention employ the administration of AAT in the form of an aerosol produced by nebulizing a ready-to-use sterilized liquid composition comprising highly pure, active AAT.

Various types of nebulizers may be used to form an aerosol containing AAT, providing the nebulizer can deliver high enough amounts of active AAT to exert its therapeutic activity.

Preferably, the activity of AAT after nebulization remains at above 90% of its activity before nebulization and no dimers, oligomers or aggregates are formed in the AAT aerosol as a result of the nebulization process. In addition, large aerosol droplets tend to deposit mainly in the larynx and upper airways. For maximal uptake in the peripheral lung regions, including lung alveoli, the mass radian diameter of the droplets (calculated from the droplet size distribution determined by laser diffraction measurements), should be less than 5 µm.

The purified, active AAT provided by the Applicant of the present invention is highly suitable for use with nebulizing means. In addition, a liquid formulation is convenient, and provides improved dosing accuracy compared to lyophilized products.

According to one embodiment, the AAT-containing liquid pharmaceutical composition is a ready-to-use liquid composition. According to another embodiment, the liquid composition is obtained by reconstituting a powder preparation of AAT into a liquid medium. According to one currently preferred embodiment, the liquid composition is a ready-to-use liquid composition, comprising a purified, stable AAT.

According to certain embodiments, the concentration of the AAT in the pharmaceutical composition is in the range of 5 to 100 mg/ml (0.5-10% weight/volume, w/v). According to additional embodiments, at least 50% of the loaded nominal dose of AAT can be delivered to the subject. Preferably 60%, and more preferably 70% or more of the AAT is delivered to the subject.

According to one embodiment, the subject is a human subject. The human subject may be an adult, a child or an infant.

The frequency of AAT treatment and the duration of each inhalation will depend both on characteristics of the treated individual (age, weight, etc.) as well as on the characteristics of the pulmonary disease to be treated. According to certain embodiments, the inhalation duration is from about 5 minutes to about 15 minutes, preferably about 10 minutes. According to other embodiments, the treatment is administered at least once a week during the exacerbation. According to yet further embodiments, the treatment is administered at least twice a week, preferably at least once a day, more preferably at least twice a day during the exacerbation.

According to certain embodiments, administering AAT during an exacerbation episode according to the teaching of the present invention is performed in combination with at least one additional therapy. According to one embodiment, the additional therapy is selected from the group consisting of antibiotic therapy, administration of bronchodilators and anti-inflammatory therapy other than AAT therapy. According to another currently preferred embodiment, the additional therapy is intravenous administration of AAT.

These and other objects, features and advantages of the present invention will become clear from the following description.

DETAILED DESCRIPTION OF THE INVENTION

Definitions

As used herein, the term "Alpha-1 Antitrypsin" (AAT) refers to a glycoprotein produced by the liver and secreted into the circulatory system. AAT belongs to the Serine Proteinase Inhibitor (Serpin) family of proteolytic inhibitors. This glycoprotein consists of a single polypeptide chain containing one cysteine residue and 12-13% of the total molecular weight of carbohydrates. AAT has three N-glycosylation sites at asparagine residues 46, 83 and 247, which are occupied by mixtures of complex bi- and triantennary glycans. This gives rise to multiple AAT isoforms, having isoelectric point in the range of 4.0 to 5.0. The glycan monosaccharides include N-acetylglucosamine, mannose, galactose, fucose and sialic acid. AAT serves as a pseudo-substrate for elastase; elastase attacks the reactive center loop of the AAT molecule by cleaving the bond between methionine358-serine359 residues to form an AAT-elastase complex. This complex is rapidly removed from the blood circulation. AAT is also referred to as "alpha-1 Proteinase Inhibitor" (API). The term "glycoprotein" as used herein refers to a protein or peptide covalently linked to a carbohydrate. The carbohydrate may be monomeric or composed of oligosaccharides.

As used herein, the terms "exacerbation" "exacerbation period" and "exacerbation episode" are used interchangeably to describe an increase in the severity of symptoms during a course of a disease, which is mostly associated with a worsening of quality of life. Exacerbations are quite frequent in patients with chronic lung diseases in general and in AAT deficient patients in particular. By definition, exacerbations are worsening and/or increase in severity and/or magnitude of the pulmonary disease symptoms.

As used herein, the term "chronic obstructive pulmonary disease" abbreviated "COPD", refers to a disease state characterized by airflow limitation that is not fully reversible. The airflow limitation is usually both progressive and associated with an abnormal inflammatory response of the lungs to noxious particles or gases. COPD is the fourth leading cause of death in America, claiming the lives of 120,000 Americans in 2002, with smoking being a primary risk factor. A diagnosis of COPD exacerbation is considered when there is increases dyspnea, increased sputum volume, and increased sputum purulence. Severity of an exacerbation can be quantified by assessing the magnitude of theses three symptoms (Dewan NA 2002. Chest 122:1118-1121).

The terms "treat" and "treating" includes alleviating, ameliorating, halting, restraining, slowing or reversing the progression, or reducing the severity of pathological conditions described above.

The terms "pulmonary delivery" and "respiratory delivery" refer to delivery of AAT to a subject by inhalation through the mouth and into the lungs.

As used herein, the terms "cystic fibrosis" or "CF" refer to an inherited autosomal recessive disorder caused by mutations in the gene encoding the cystic fibrosis transmembrane conductance regulator (CFTR) chloride channel.

The term "emphysema" as is used herein refers to a pathological condition of the lungs in which there is a decrease in respiratory function and often breathlessness due to an abnormal increase in the size of the air spaces, caused by irreversible expansion of the alveoli and/or by the destruction of alveolar walls by neutrophil elastase.

The term "bronchiectasis" refers to a congenital or acquired disorder associated with abnormal bronchial dilatation with bronchial wall destruction and transmural inflammation. The most important functional finding of the altered airway anatomy is severely impaired clearance of secretions from the bronchial tree.

As used herein, the term "sarcoidosis" refers to a disease characterized by the formation of granulomatous lesions that appear especially in the liver, lungs, skin, and lymph nodes.

"Tuberculosis" or "TB" as used herein refers to the disease caused by the *Mycobacterium tuberculosis* bacterium. TB is an airborne, chronic bacterial infection.

The present invention relates to methods for treating exacerbation episodes of pulmonary diseases, by administering to a subject in need thereof a therapeutically effective amount of Alpha-1-antitrypsin. As described herein, the present invention relates to various pulmonary diseases, which may or may not be associated with AAT deficiency, each having its own symptoms and characteristics. However, in most cases, exacerbation episodes are associated with inflammation, which, in turn, may cause an imbalance between proteinases and antiproteinases, leading to the destruction of the lung matrix. The AAT administered directly to the lung according to the teaching of the present invention can overcome the imbalance of proteinase (elastase)/antiproteinase (AAT), thus preventing the damage caused to the lungs. Such imbalance may be the results of congenital deficiency in AAT, or in non-deficient subjects where the imbalance is due to a severe inflammation which can be regulated only by external insertion of greater quantities of antiproteinase (AAT).

Emphysema and AAT Deficiency

Emphysema is a pathological condition of the lungs marked by an abnormal increase in the size of the air spaces, resulting in strenuous breathing and an increased susceptibility to infection. It can be caused by irreversible expansion of the alveoli or by the destruction of alveolar walls. Due to the damage caused to lung tissue, elasticity of the tissue is lost, leading to trapped air in the air sacs and to impairment in the exchange of oxygen and carbon dioxide. In light of the walls breakdown, the airway support is lost, leading to obstruction in the airflow. Emphysema and chronic bronchitis frequently co-exist together to comprise chronic obstructive pulmonary disease (COPD). Congenital emphysema, also known as Alpha-1 Antitrypsin (AAT) deficiency or inherited emphysema is a genetic disorder that increases the risk of developing a variety of diseases including pulmonary emphysema and cirrhosis of the liver. It is caused by mutation in the gene coding for the 52 kDa glycoprotein alpha-1-antitrypsin, the body major serine proteinase inhibitor or serpin. This gene is located in the long arm of chromosome 14 of the human genome. The genetic deficiency can result in life-threatening liver disease in children and adults or in lung disease in adults. In its classic form, an inherited mutation of the AAT gene causes an abnormal build up of AAT within the hepatocytes of the liver. The liver is the major source of circulating AAT and this transport problem leads to low levels of AAT in the blood and tissue. Various mutations of the AAT gene exist, most of them associated with deficiency in circulating AAT. Some genotypes lead to the production of dysfunctional proteins which increase the risk of emphysema, but is released at a normal level to the circulation.

It has been estimated that in the US only, there are approximately 100,000 severely deficient individuals and about 25 million carriers of at least one deficient gene for AAT, and similar number have been suggested for the European population (Sandhaus 2004, supra). The classic proteinase pathogenesis model of congenital emphysema was based on failure of the body to neutralize elastase-related enzymatic activity, the elastase being released from polymorphonuclear leukocytes attracted to the lung alveoli during infections. Based on the nature of the triggering event and the cellular physiology of AAT as an elastase inhibitor it has been recently suggested that AAT also functions as an acute-phase reactant: during exacerbation periods, particularly exacerbations related to lung infections, higher levels of circulating enzyme inhibitors are required, and these are supplied by induction of acute phase reactants, among which AAT is prominent.

Cystic Fibrosis

The membrane defect caused by the CFTR mutation leads to chronic lung inflammation and infection. Chronic lower respiratory infection provokes a persistent inflammatory response in the airway, resulting in chronic obstructive disease. As pulmonary reserves decrease, CF patients become prone to episodes of exacerbation, characterized by worsening symptoms of respiratory infection, particularly by *Pseudomonas aeruginosa*, accompanied by acute decline in lung function.

Loss of pulmonary function is a primary cause of death in patients suffering from cystic fibrosis. Patients with a Forced Expiratory Volume in one second (FEV1) below 30% of their predicted value have a 2-year mortality of greater than 50%. The current mortality rate is 1.2 deaths per 100 patients per year; the median survival is 32 years. Of the deaths in which a case was specified, 94% were due to cardiorespiratory failure. Respiratory failure is characterized by increasing dyspnea, hypoxemia and elevation of arterial $PCO_2$. During their lifetime, CF patients are restricted in their day-to-day activities due to reduced lung function and constant pulmonary infections as a result of their condition.

One of the major side effects of chronic infection associated with CF is the chronic presence of phagocytic neutrophils in the lungs in response to bacterial infections and the release of various chemoattractants. These leukocytes secrete elastase, which has the potential to destroy the elastic tissue of the lung. In addition, neutrophils of patients with CF have been shown to be in a state of increased responsiveness and tend to degranulate more readily, releasing tissue-destroying elastase. Thus, patients with CF appear to have a state of unregulated inflammatory response, which overwhelms the normal protease (elastase)/antiprotease (AAT) balance, leading to the accumulation of elastase in the lung and ultimately to tissue damage.

Previous studies have shown that much of the pulmonary damage in CF results from the presence of unneutralized elastase and other proteases. The abnormal cycle is destructively self-perpetuating and self-expanding: increased elastase leads to the recruitment of more neutrophils to the lung that in turn secrete additional proteases. This cycle further overwhelms the natural normal protease (elastase)/antiprotease balance leading to destruction of the lung architecture, severe pulmonary dysfunction and ultimately death. It has been suggested that supplement of AAT to CF patient may reduce the deleterious effects associated with excessive amounts of elastase. Supplemental AAT is particularly important during episodes of exacerbation, which are associated with severe inflammation symptoms.

Preferably, AAT is administered to CF patients by the inhalation route. It has been previously demonstrated (McElvaney et al, 1991) that aerosolized alpha-antitrypsin given to cystic fibrosis patients suppressed neutrophil elastase in the respiratory epithelial lining fluid (ELF), restored the anti-neutrophil elastase capacity in the ELF and reversed the inhibitory effect of the ELF on the ability of neutrophils to effectively combat *Pseudomonas* infection. Advantageously, aerosol formulations can be readily produced using the AAT liquid preparation disclosed by the Applicant of the present invention. Moreover, the aerosolized AAT formulation administered by inhalation is highly suitable for treating exacerbations in the pulmonary dysfunction associated with CF, as it is fast and easy to apply.

Bronchiectasis

Bronchiectasis is an abnormal and irreversible dilation of the proximal medium-sized bronchi (>2 mm in diameter) caused by destruction of the muscular and elastic components of the bronchial walls. It can be congenital or acquired.

Congenital bronchiectasis usually affects infants and children and results from developmental arrest of the bronchial tree. The more commonly acquired forms occur in adults and older children and are associates with an infectious insult, impairment of drainage, airway obstruction, and/or a defect in host defense. The damage to the muscular and elastic components of the bronchial wall results from the inciting infectious agent and from the host response. The latter may be mediated in part by inflammatory cytokines, nitric oxide, and neutrophilic proteases. Additionally, peribronchial alveolar tissue may be damaged, resulting in diffuse peribronchial fibrosis.

The result is abnormal bronchial dilatation with bronchial wall destruction and transmural inflammation. The most important functional finding of altered airway anatomy is severely impaired clearance of secretions from the bronchial tree.

Frequent exacerbations of bronchiectasis are often associated with infection and symptoms of increased dyspnea, wheeze, and sputum production. It has been suggested that during exacerbation of bronchiectasis, particularly in infective episodes, neutrophils are predominant in necrosis pathways, which may lead to increased levels of proteolytic agents. These agents participate in destruction of lung matrix and contribute to the development of bronchiectasis. Thus, administering AAT according to the methods of the present invention is highly suitable for treating exacerbation periods of bronchiectasis.

Tuberculosis

Tuberculosis (TB) has recently reemerged as a public health problem. Most persons that are infected with *Mycobacterium tuberculosis* harbor the bacterium without symptoms but many develop active TB disease. Each year, 8 million people worldwide develop active TB and 3 million die.

Cases of TB dropped rapidly in the 1940s and 1950s when the first effective antibiotic therapies for TB were introduced. In 1985 the number of active TB cases in the United States began to rise again. Several forces, often interrelated, were behind TB's resurgence. For example, individuals with HIV/AIDS are particularly vulnerable to active TB.

The problem of multi drug resistance of *M. tuberculosis* is another factor in the reemergence of the disease. Multidrug-resistant TB (MDR-TB) is much more difficult to cure. Treatment for MDR-TB often requires the use of special TB drugs, all of which can produce serious side effects. To cure MDR-TB, patients may have to take several antibiotics, at least three to which the bacteria still respond, every day for up to two years. However, even with this treatment, about 40% of MDR-TB will die, which is the same as for patients with standard TB who do not receive treatment. Palliative therapy for these patients is needed.

Preparation of AAT

According to one aspect of the present invention a purified stable composition of AAT is provided. Preferably, a liquid composition of purified, stable AAT is provided. International application WO 2005/027821, to the applicant of the present invention, provides pharmaceutical compositions comprising a purified, stable, active AAT in a form of a ready to use sterile solution. WO 2005/027821 also provides process, which combines removal of contaminating substances (i.e., lipids, lipoproteins and other proteins) and separation of active from inactive AAT by sequential chromatography steps. The process disclosed in that invention is highly suitable for a large-scale production of AAT, in the range of tens of kilograms or more.

The mixture of proteins from which the AAT is purified is preferably Cohn Fraction IV-1 paste, but can include other Cohn Fractions, separately or in combination; human blood plasma; plasma fractions; or any protein preparation containing AAT. For instance, the process is applicable to purification of recombinant human AAT from the milk of transgenic animals.

In that application, the mixture of proteins comprising AAT is dispersed in an aqueous medium, preferably water, at a ratio of about 20 to about 35 liter per about 1 kg of source material, preferably Cohn Fraction IV-1 paste. The pH of the dispersion is adjusted to a pH range of from about 8.0 to about 9.5. The pH adjustment stabilizes the AAT and promotes the dissolution of the AAT in the dispersion, thereby increasing the production yield. Dispersion may take place at an elevated temperature of between 30° C. and 40° C., for further increase in AAT solubility.

A particular advantage of that process is the elimination of contaminants or by-products that otherwise compromise the efficiency of AAT purification processes. In particular, Cohn Fraction IV-1 paste preparations contain a significant amount of the lipoprotein Apo A-1, which has the effect of compromising column flow and capacity during purification. Other non-desired proteins such as albumin and transferrin are also present in the paste preparation. Removing a portion of such contaminants according to invention disclosed in WO 2005/-27821 is performed by two steps: (a) removing contaminating lipids and lipoproteins by lipid removal agent and (b) precipitating a portion of contaminating protein from the AAT-containing aqueous dispersion. The removal of contaminating proteins, without loss of AAT, enables a significant reduction in equipment scale, e.g., column size.

The precipitate that forms can be separated by conventional means such as centrifugation or filtration, and is then discarded. The supernatant is ready for further purification, for example an anion exchange resin. The AAT is then eluted from the column. The solution is treated to reduce its water content and change the ionic composition by conventional means such as by diafiltration, ultrafiltration, lyophilization, etc., or combinations thereof.

According to one embodiment, the AAT-containing effluent obtained after the first anion exchange chromatography is concentrated by ultrafiltration. The retentate is then diafiltered against pure water to reach conductivity within the range of from about 3.5 to about 4.5 mS/cm.

To further purify the AAT-containing solution obtained after the first anion exchange chromatography the solution is loaded on a cation exchange resin with the same type of buffer used for the anion-exchange step, having appropriate pH and conductivity such to allow the AAT to pass and be washed off with the buffer flow through, while contaminating substances are retained on the cation exchange resin.

The AAT-containing solution obtained after the cation exchange chromatography can be treated to reduce its water content. According to one embodiment, the solution is concentrated by ultrafiltration.

The ion-exchange chromatography is also used to separate active AAT from inactive AAT. That invention further comprises methods for separating active AAT from other contaminating substances, including solvent/detergent compounds used for viral inactivation. Such separation is achieved by the second anion exchange chromatography. The AAT eluted from the second anion exchange chromatography step is therefore not only highly active, but also highly pure.

Throughout the process of that invention only one type of buffer is used, with adjustment of pH and conductivity as required throughout the various process steps. According to one embodiment, the buffer is any suitable acid/salt combination that provides acceptable buffer capacity in ranges of pH required throughout the process. According to preferred embodiments the process uses a buffer other than citrate-based buffer. According to yet other embodiments, the buffer anion is acetate.

According to one embodiment, the process of that invention further comprises viral removal and/or viral inactivation steps. Methods for viral removal and inactivation are known in the art.

One method for viral removal is filtration, preferably nanofiltration, removing both enveloped and non-enveloped viruses. According to one embodiment, the viral removal step comprises filtration. According to another embodiment, the virus removal step is performed after the cation exchange chromatography. Typically, the cation exchange flow-through solution containing AAT is concentrated, and then nanofiltered.

According to one embodiment, the method of viral inactivation employed comprises a solvent/detergent (S/D) treatment. The viral inactivation step is preferably performed prior to loading the solution on the second anion exchange resin. According to one embodiment, the detergent used is polysorbate and the solvent is Tri-n-Butyl-Phosphate (TnBP). According to another embodiment, the polysorbate is polysorbate 80. According to one embodiment Polysorbate 80 may be added from about 0.8% to about 1.3% volume per weight (v/w) of the resulting mixture and TnBP may be added from about 0.2% to about 0.4% weight per weight of the resulting mixture.

The solution containing active, purified AAT obtained after the second anion exchange chromatography can be further processed to obtain a pharmaceutical composition for therapeutic, diagnostic, or other uses. To prepare the product for therapeutic administration the process further comprises the steps of changing the ionic composition of the solution containing purified, active AAT to contain a physiologically compatible ion and sterilizing the resulted solution.

The purified AAT obtained by the process of that invention is highly stable.

According to one embodiment, the pharmaceutical composition comprises at least 90% pure, preferably 95% pure, more preferably 99% pure AAT. According to another embodiment, at least 90% of the AAT is in its active form.

Pharmaceutical Compositions and Methods of Treatment

The term "pharmaceutical composition" is intended to be used herein in its broader sense to include preparations containing a protein composition in accordance with this invention used for therapeutic purposes. The pharmaceutical composition intended for therapeutic use should contain a therapeutic amount of AAT, i.e., that amount necessary for preventative or curative health measures.

As used herein, the term "therapeutically effective amount" refers to an amount of a protein or protein formulation or composition which is effective to treat a condition in a living organism to whom it is administered over some period of time.

Pharmaceutical compositions of the present invention may be manufactured by processes well known in the art, e.g. by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more acceptable diluents or carriers comprising excipients and auxiliaries, which facilitate processing of the active compounds into preparations, which can be used pharmaceutically. Proper formulation is dependent on the route of administration chosen. According to certain currently preferred embodiments, the pharmaceutical compositions of the present invention are formulated in a form suitable for inhalation.

The AAT-containing pharmaceutical compositions disclosed in WO 2005/027821 to the Applicant of the present invention is advantageous over hitherto known AAT-containing preparations, as the AAT is highly stable also when the composition is kept in a liquid from. Therefore, it is not necessary to lyophilize the AAT preparation for stable storage in a form of a powder. Subsequently, there is no need to reinstate the powder to a liquid before use for parenteral administration or for inhalation.

According to certain currently preferred embodiments, AAT in a ready-to-use liquid formulation is used with the methods of the present invention.

It has been estimated that only 2% of the intravenously administered AAT dose reaches the lung (Hubbard and Crystal, 1990. Lung 168 Suppl:565-78, 1990). This is a major disadvantage in treating pulmonary diseases in general, and in treating exacerbation episodes in particular.

Therefore, administration of AAT by the inhalation route may be more beneficial as it reaches directly the lower respiratory tract. The inhalation route also requires lower therapeutic doses of AAT and thus the scarce supply of human plasma-derived AAT, currently being the only source for AAT, would be available for the treatment of more patients. This route of administration may be also more effective in neutralizing neutrophil elastase, and in correcting the imbalance between proteinase and anti-proteinases in the lung tissues, and is thus highly suitable for treating pulmonary diseases at periods of exacerbation. In addition, administration by inhalation is simpler and less stressful for the patient than the intravenous route and would reduce the burden on the local health care system (by requiring less clinical input).

Formulations of pharmaceutical compositions for administration by the route of inhalation are known in the art, as well as inhaler systems and devices. In general, for administration by inhalation, the active ingredients are delivered in the form of an aerosol spray from a pressurized metered dose inhaler with the use of a suitable propellant, e.g., dichlorodifluoromethane, trichlorofluoromethane, dichloro-tetrafluoroethane or carbon dioxide. The active ingredient in the aerosol spray may be in a powder form administered using a dry powder inhaler, or in aqueous liquid aerosol form using a nebulizer.

Powder inhalers are designed to be used until a given charge of active material is exhausted from the device. The charge loaded into the device will be formulated accordingly to contain the proper inhalation dose amount of AAT for delivery in a single administration. (See generally, Remington's Pharmaceutical Sciences, 18th Ed. 1990, Mack Publishing Co., Easton, Pa., Chapter 92 for information relating to aerosol administration).

Nebulizers for liquid aerosol delivery may be categorized as jet nebulizers operated by a pressurized flow of air using a portable compressor or central air supply in a hospital, ultrasonic nebulizers incorporating a piezo-crystal to provide the energy for generating the aerosol out of an ultrasonic fountain, and electronic nebulizers based on the principle of a perforated vibrating membrane.

Any of a variety of powder inhalers and nebulizers as are known in the art can be used for AAT administration according to the teachings of the present invention.

For example, U.S. Pat. No. 6,655,379 discloses methods and devices for delivering an active agent formulation to the lung of a human patient. The active agent formulation may be in dry powder form, it may be nebulized, or it may be in admixture with a propellant. According to the teaching of that patent, the active agent formulation, particularly insulin, is delivered to a patient at an inspiratory flow rate of less than 17 liters per minute.

Methods regarding the delivery of AAT formulations using nebulizers are discussed, for example, in U.S. Pat. Nos. 5,093,316, 5,618,786 and 5,780,440.

The Applicant of the present invention and co-workers disclosed the use of eFlow® nebulizer, disclosed in International Patent Application WO 01/34232, for AAT delivery to the lung. The eFlow® nebulizer provides an increased amount of aerosol during inhalation while minimizing both aerosol losses during exhalation and the residual drug in the nebulizer reservoir. The nebulizer includes an aerosol generator that atomizes the liquid through a vibrating diaphragm into particle sizes that are efficiently delivered to the lungs.

The operating conditions for delivery of a suitable inhalation dose will vary according to the type of mechanical device employed. For some aerosol delivery systems, such as nebulizers, the frequency of administration and operating period will be dictated chiefly by the amount of the active composition (AAT according to the present invention) per unit volume in the aerosol. Typically, the higher the concentration of the protein in the nebulizer solution the shorter is the operating period. Some devices such as metered dose inhalers may produce higher aerosol concentrations than others and thus will be operated for shorter periods to give the desired result.

According to certain embodiments, the methods of the present invention employ a nebulizer comprising a ready-to-use inhalation solution comprising therapeutically effective amount of AAT.

According to currently certain preferred embodiments, the ready-to-use liquid pharmaceutical composition is packed in pre-sterilized unit dose vials containing 0.25 ml-10 ml, preferably 0.25 ml to 5 ml, commonly used for ready to use inhalation solutions. The vial can be made of glass or polymeric materials or the liquid can be filled into polyethylene or any other suitable polymer vials, manufactured for instance by a blow fill seal process According to other preferred embodiments, at least 60% of the nebulized dose is dissolved in droplets having a diameter of 5 μm or less. Such droplet size enhances the AAT delivery to the alveolar regions, where its activity is mostly required. According to certain embodiments, at least 50%, preferably 60% and more preferably 70% or more of the loaded nominal dose of AAT can be delivered to the subject.

According to the teaching of the present invention, AAT is administered during exacerbation episodes of various pulmonary diseases. As described hereinabove, the pulmonary disease may be associated with an inherited deficiency in AAT, in such case patients typically receive intravenous augmentation therapy of AAT. Thus, according to certain embodiments, the method of the present invention comprises administering to a subject in need thereof a therapeutic amount of AAT via inhalation in combination with administering the AAT intravenously.

Typically, during exacerbation periods, the inhaled AAT is administered for relatively short periods of time. According to certain embodiments, the inhalation time is between about 5-15 minutes, preferably about 10 minutes. The AAT may be administered once a week or administration can be repeated at least twice a week, each day or even twice a day.

The progressive course of COPD is complicated by exacerbations that have many causes and occur with increasing frequency as the disease progresses. During exacerbation episodes there is an increase in the severity of the pulmonary disease symptoms, which are associated with a worsening of quality of life, particularly to AAT deficient patients. COPD exacerbations are characterized by increased dyspnea, resulting from obstruction of the patient's airway accompanied by increases in coughing, sputum production, purulence and wheezing. Exacerbations are well correlated with long-term deterioration of lung function, which is another characteristic of COPD.

The AAT protein is an acute phase reactant protein and, as such, its synthesis is amplified during episodes of inflammation or stress (Sandhaus RA. α1-Antitrypsin deficiency *6: New and emerging treatments for α1-antitrypsin deficiency. Thorax 59:904-909, 2004), which particularly occurs in exacerbation periods. AAT deficient patients risk severe lung damage during exacerbation periods, due to the inability to mount an effective acute phase AAT elevation. During acute exacerbation periods such shortage of AAT may also occur in normal individuals, resulting in the excess of neutrophil elastase leading to destruction of lung tissues. Addition of a therapeutically significant amount of AAT directly to the lung tissue as disclosed by the present invention satisfies the clinical need for a treatment that provides an adequate answer to the patient's condition and prevents the potential accelerated decline in the disease state due to the exacerbation.

The principles of the invention may be better understood with reference to the non-limiting examples below.

EXAMPLES

Example 1

Treatment of AAT-Deficient Patients During Periods of Disease Exacerbations

This example describes a placebo-controlled, double blind, randomized, multicenter trial of inhaled, nebulized AAT. The trial objective is to assess safety and efficacy of inhaled AAT in the treatment of emphysema secondary to lung disease by evaluating exacerbations periods in comparison to steady state periods with no exacerbations.

AAT is administered as supplementary therapy during exacerbations to subjects suffering from COPD, which may be AAT-deficient or AAT-normal subjects. The AAT applied is plasma-derived, human AAT, produced by the Applicant of the present invention, Kamada Ltd. (Israel). AAT is administered using a nebulizer, for example a dedicated electronic, small size nebulizer that aerosolizes liquid medications via a vibrating, perforated membrane.

100-250 subjects are enrolled into in the two arm study, randomized to receive either AAT or placebo, respectively. The expected study duration is around 12-36 months. Subjects enrolled to the study may be AAT-deficient patients with the Pi genotypes ZZ, Z null, or other severely deficient genotypes having baseline AAT levels of <11 μM, or patients suffering from COPD that are not AAT-deficient.

Only patients meeting all of the following main inclusion criteria are entered into the study:
1. Able and willing to sign informed consent.
2. At least 18 years of age.
3. Have Forced Expiratory Volume in one second (FEV1) <80% of predicted value post-bronchodilator.
5. Able to comply with study procedures.
6. Willing to comply with standardized treatment of exacerbations of lung disease.

Subjects are excluded from the study according to the following criteria:
1. FEV 1<20% of predicted value post-bronchodilator.
2. Have history of lung transplant.
3. Experienced any lung surgery within the past 2 years.
4. Are on any thoracic surgery waiting list.
5. Have clinically significant liver disease.
6. Have severe concomitant disease (serious malignant disease, congestive heart failure NYHA III/IV, clinically significant pulmonary fibrosis).
7. Experienced active pulmonary infection/exacerbation within the last month.
8. Are active smokers during the last 6 months, or blood CO values are indicative of ongoing smoking habit.
9. Are pregnant or lactating.
10. Women of child-bearing potential not taking adequate contraception.
11. Have any medical condition which the investigator feels will prohibit the patient from completing the trial.
12. Participate in another clinical trial within 30 days prior to inclusion at baseline.

Subjects receive the predetermined dose of inhaled AAT or equivalent volume of placebo for a predetermined period, beginning within a set interval of the onset of exacerbations of lung disease.

The investigational product and control product are administered by inhalation.

The primary endpoint of the study is selected from the following: progression of emphysema as determined by CT lung density and lung function tests, frequency of exacerbation/year, severity of exacerbation, time-length of exacerbations and questionnaire scores.

The Secondary endpoints include safety data, adverse affects, airway inflammation assessment by sputum analysis, lung functions, quality-of life (QoL), urine Desmosine.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating an exacerbation of a pulmonary disease, which comprises administering to the lungs of a subject via inhalation at the time of an exacerbation episode a therapeutically effective amount of a pharmaceutical composition comprising purified Alpha-1 antitrypsin (AAT), wherein the pharmaceutical composition is a ready-to-use, aqueous sterile solution and the purified AAT is at least 90% pure and at least 90% of the AAT is in its active form and further wherein at least 50% to 70% of the loaded nominal dose of AAT is delivered to the subject, thereby alleviating imbalanced proteinase/antiproteinase ratios which develop during the exacerbation period.

2. The method according to claim 1, wherein the pulmonary disease is associated with an AAT-deficiency and is selected from the group consisting of emphysema; chronic obstructive pulmonary disease (COPD); bronchiectasis; parenchymatic and fibrotic lung diseases or disorders; cystic fibrosis, interstitial pulmonary fibrosis and sarcoidosis; and tuberculosis and lung diseases and disorders secondary to HIV.

3. The method according to claim 2, wherein the pulmonary disease is COPD, emphysema or congenital emphysema.

4. The method according to claim 1, wherein the AAT is naturally occurring AAT purified from an unpurified mixture of proteins by a process comprising of chromatography on a plurality of ion exchange resins, comprising a first anion exchange resin followed by a cation and a second anion exchange resins.

5. The method according to claim 1, wherein the pharmaceutical composition is devoid of a stabilizer.

6. The method according to claim 5, wherein the pharmaceutical composition is in the form of an aerosol spray or a liquid pharmaceutical composition in which an aerosol is produced by a nebulizer.

7. The method according to claim 6, wherein the activity of the aerosolized AAT remains at above 90% of the AAT activity before aerosolization.

8. The method according to claim 6 wherein the aerosol droplets have a mass radian diameter that is less than about 5 μm.

9. The method according to claim 6, wherein the AAT concentration in the solution to be aerosolized is 0.5% to 10% w/v.

10. The method according to claim 2, wherein the AAT is administered at a regime selected from the group consisting of at least once a week, at least twice a week and at least once a day.

11. A method for treating an exacerbation of a pulmonary disease, which comprises administering to the lungs of a subject via inhalation at the time of an exacerbation episode a therapeutically effective amount of a pharmaceutical composition comprising purified Alpha-1 antitrypsin (AAT), wherein the pharmaceutical composition is a ready-to-use, aqueous sterile solution and the purified AAT is at least 90% pure and at least 90% of the AAT is in its active form and further wherein at least 50% to 70% of the loaded nominal dose of AAT is delivered to the subject to alleviate the acute imbalance in proteinase/antiproteinase ratio developed during the exacerbation period, wherein the AAT is administered in combination with at least one additional therapy for treatment of the pulmonary disease.

12. The method according to claim 11, wherein the additional therapy is selected from the group consisting of an antibiotic therapy, administration of bronchodilators and anti-inflammatory therapy other than AAT therapy.

13. The method according to claim 11, wherein the additional therapy is intravenous administration of AAT.

14. The method according to claim 1, wherein the subject is a human subject.

15. A method for treating a chronic or non-chronic pulmonary disease in a subject in need of such treatment, wherein the subject is already receiving treatment for the pulmonary disease, which comprises treating an exacerbation of the pulmonary disease by administering to the lungs of the subject via inhalation at the time of the exacerbation episode a therapeutically effective amount of pharmaceutical composition comprising purified Alpha-1 antitrypsin (AAT), wherein the pharmaceutical composition is a ready-to-use, aqueous sterile solution and the purified AAT is at least 90% pure and at least 90% of the AAT is in its active form and further wherein at least 50% to 70% of the loaded nominal dose of AAT is delivered to the subject, thereby alleviating imbalanced proteinase/antiproteinase ratios which develop during the exacerbation period.

* * * * *